United States Patent
Norton et al.

(10) Patent No.: US 7,544,218 B2
(45) Date of Patent: Jun. 9, 2009

(54) METHOD FOR FABRICATING A MEDICAL DEVICE THAT INCLUDES A CAPACITOR THAT DOES NOT REQUIRE OXIDE REFORMATION

(75) Inventors: John D. Norton, New Brighton, MN (US); Joachim Hossick-Schott, Minneapolis, MN (US); Mark Edward Viste, Brooklyn Center, MN (US); Brian John Melody, Greer, SC (US); John Tony Kinard, Greer, SC (US)

(73) Assignees: Kemet Electronics Corporation, Greenville, SC (US), part interest; Medtronic, Inc., Minneapolis, MN (US), part interest ( * ) Notice: Subject to any disclaimer, the term of this patent is extended or adjusted under 35 U.S.C. 154(b) by 514 days.

(21) Appl. No.: 11/407,306

(22) Filed: Apr. 19, 2006

(65) Prior Publication Data
US 2006/0187616 A1    Aug. 24, 2006

Related U.S. Application Data

(62) Division of application No. 10/448,594, filed on May 30, 2003, now abandoned.

(51) Int. Cl.
*H01G 9/04* (2006.01)
(52) U.S. Cl. ................ 29/25.03; 29/25.41
(58) Field of Classification Search ............ 361/509
See application file for complete search history.

(56) References Cited

U.S. PATENT DOCUMENTS

| | | | |
|---|---|---|---|
| 5,716,511 A | 2/1998 | Melody et al. | 205/324 |
| 5,861,006 A | 1/1999 | Kroll | 607/5 |
| 5,899,923 A | 5/1999 | Kroll et al. | 607/5 |
| 6,096,062 A | 8/2000 | Silvian | 607/5 |
| 6,219,222 B1 | 4/2001 | Shah et al. | 361/506 |
| 6,283,985 B1 | 9/2001 | Harguth et al. | 607/1 |
| 6,409,905 B1 | 6/2002 | Melody et al. | 205/234 |
| 6,480,371 B1 | 11/2002 | Kinard et al. | 361/508 |
| 6,850,405 B1 | 2/2005 | Mileham et al. | 361/302 |
| 2001/0047190 A1 | 11/2001 | Harguth et al. | 607/1 |
| 2002/0095186 A1 | 7/2002 | Harguth et al. | 607/5 |
| 2003/0088273 A1 | 5/2003 | Liu et al. | 607/2 |

FOREIGN PATENT DOCUMENTS

WO      WO01/57292      8/2001

OTHER PUBLICATIONS

International Search Report, PCT/US2004/017059, Nov. 15, 2004, Kurze.

*Primary Examiner*—Stephen W Smoot
(74) *Attorney, Agent, or Firm*—Joseph T. Guy; Nexsen Pruet, LLC

(57) ABSTRACT

A therapeutic medical device system comprising an electrolytic capacitor including an anode, cathode and an electrolyte. The anode is anodized in an electrolyte comprises an aqueous solution of alkanol amine, phosphoric acid and an organic solvent preferably defined by formula 1:

$$CH_3-(OCH_2CH_2)_m-OCH_3 \qquad \text{Formula 1}$$

wherein m is an integer from 3 to 10.

19 Claims, 1 Drawing Sheet

METHOD FOR FABRICATING A MEDICAL DEVICE THAT INCLUDES A CAPACITOR THAT DOES NOT REQUIRE OXIDE REFORMATION

CROSS REFERENCE TO RELATED APPLICATION

This application is divisional application of U.S. patent application Ser. No. 10/448,594 filed May 30, 2003 which is abandoned and is related to prior non-provisional patent application filed 7 May 2003 by Norton et al. bearing Ser. No. 10/431,356 and entitled, "Wet Tantalum Reformation Method and Apparatus" the contents of which are hereby incorporated herein.

BACKGROUND OF THE INVENTION

The present invention relates primarily to improved capacitors; in particular, the present invention relates to electrochemical apparatus and especially medical devices, both implantable and external to a patient, comprising capacitors that do not require reformation of the oxide. An apparatus incorporating such improved capacitors exhibits extended battery life and/or smaller size as compared to a prior art apparatus using capacitors that require or benefit from periodic reforming of degraded oxide.

Medical devices, and in particular implantable medical devices, have revolutionized the practice of medicine. One critical area of advancement has been in the area of defibrillators and cardioverters. These devices detect abnormal heart rhythms and apply a therapeutic electrical charge to return the heart to a normal rhythm. In general, the devices rely on a relatively low voltage battery to charge a capacitor. At the appropriate time the capacitor discharges the stored electrical energy as a therapeutic pulse.

Battery life in implantable medical devices is a critical concern. In the event that a battery needs replacement, typically the entire device is replaced with a new device subjecting the patient to the attendant discomfort of this invasive procedure. It would be apparent that any extension of battery life would be highly desirable under all circumstances. It is therefore the ultimate desire to extend battery life as much as possible. In lieu of or in addition to extending battery life, reducing the overall device volume of implantable and other medical devices is also highly desirable.

It has long been realized that one limitation to extending battery life is degradation of the capacitor. It has long been realized that capacitors degrade at rest. This degradation has been considered to be due to deterioration of the oxide layer. As capacitors degrade, the amount of battery power required to fully charge the capacitor increases.

There are a myriad of techniques described in the art for alleviating the problems associated with capacitor degradation. U.S. Pat. App. Publ. 2002/0095186 describes maintaining the capacitor at high voltage for about five minutes before discharging through a non-therapeutic load. This is contrary to battery longevity since this charge/discharge sequence provides no useful therapeutic purpose. U.S. Pat. No. 6,096,062 describes a method for testing the leakage current prior to charging the capacitor to peak voltage. The testing and charging, again, represent non-therapeutic battery use that unnecessarily limits the battery life. U.S. Pat. No. 5,899,923 describes a process to set the capacitor reformation interval based on an estimated charge time calculated from measurable electrical parameters. U.S. Pat. No. 5,861,006 describes a process to set the capacitor reformation interval based on the charge time history of the device. U.S. Pat. No. 6,283,985 describes charging and discharging the capacitor through non-therapeutic channels. U.S. Pat. App. Publ. 2001/0047190 describes charging/discharging techniques.

While these techniques are beneficial, they all utilize battery capacity for maintenance thereby robbing battery capacity that would be more beneficially used for therapy. Reducing, or eliminating, non-therapeutic charging of the capacitors would greatly extend the life of existing batteries. It has long been a desire to provide a capacitor that does not require reformation or a maintenance voltage.

Electrolytic capacitors, particularly tantalum-based capacitors, have been prepared utilizing aqueous solutions of ethylene glycol with ionogens such as acetic acid, phosphoric acid and ammonium acetate. Capacitors of this type are exemplified in U.S. Pat. No. 6,219,222. While these capacitors have historically fulfilled many of the necessary requirements they are deficient in their ability to meet the increasing demands related to stabilized oxide layers. The oxide layer in these ethylene glycol based capacitors degrade therefore making them undesirable for use in implantable medical devices for the reasons set forth previously herein.

It has been realized by the inventors, through diligent research, that the degradation in leakage current is associated with re-hydration of the layer of polyphosphate covering the anodic oxide layer upon standing, not physical degradation of the oxide, as previously thought. Phosphoric acid is relied on to improve chemical stability of the oxide layer.

Even with this advanced understanding the dilemma remained for the artisan since no suitable solution was forthcoming.

These apparently unresolved dilemmas are mitigated by the present invention. The present invention is directed to an anodizing electrolyte which mitigates the deficiencies of the prior art. These novel capacitors also have improved properties above and beyond the more highly efficient energy usage. This novel structure allows for improvements in the art of implantable medical devices with extended battery life.

BRIEF SUMMARY OF THE INVENTION

It is object of the present invention to provide devices, and in particular medical devices, having extended battery life and/or a smaller overall size for such devices.

It is another object of the present invention to provide an implantable medical device comprising capacitors which do not degrade upon resting and which do not require oxide reformation.

A particular feature of the present invention is elimination of a process which required non-therapeutic expenditure of battery capacity.

Another particular feature is elimination of deficiencies in the capacitor which greatly improve the efficiency of capacitor charging.

An embodiment of the present invention is provided in a therapeutic system comprising an implantable medical device. The implantable medical device comprises an electrolytic capacitor. The electrolytic capacitor comprises an anode, cathode and a working electrolyte.

Another embodiment is provided in a method for forming an implantable medical device comprising the steps of:
forming a capacitor comprising the steps of:
preparing a metal anode from a valve metal powder comprising anodizing the metal anode with an aqueous anodizing electrolyte comprising phosphoric acid, at least one organic solvent and alkanolamine;
providing a cathode;

activating the anode and the cathode with a working electrolyte comprising:
water, organic solvent and an ionogen;
incorporating the capacitor into a circuit; and
incorporating the circuit into an implantable medical device.

DETAILED DESCRIPTION OF THE INVENTION

Figure 1:
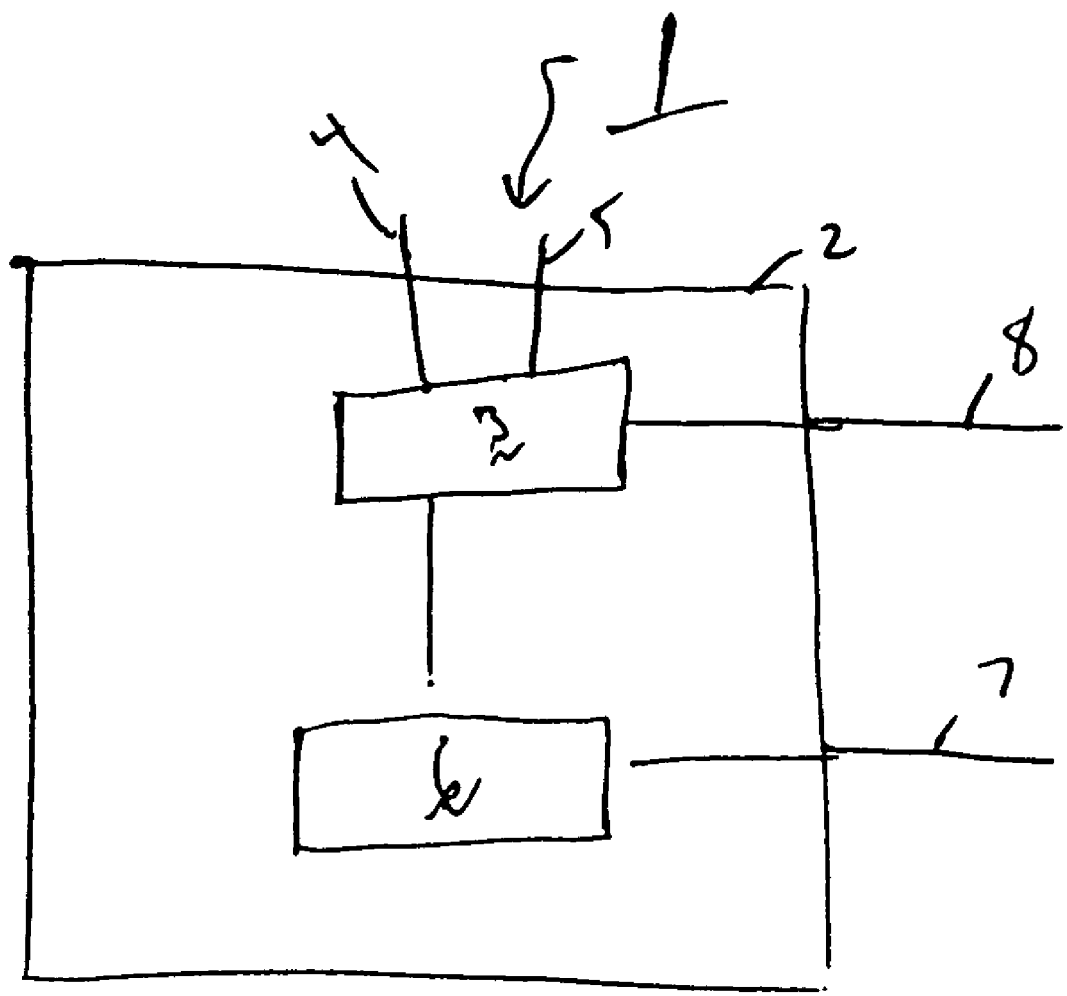
FIG. 1 is a schematic representation of a defibrillator.

The inventors have developed through diligent research an implantable medical device with greatly extended battery life. The implantable medical device comprises a capacitor wherein the capacitor comprises an anode anodized in an anodizing electrolyte comprising an aqueous solution of an alkanol amine, orthophosphoric acid and an optional organic solvent.

The invention will be described with reference to the drawings forming a part of the present disclosure and illustrating select embodiments of the present invention. Those of skill in the art will readily recognize that many other electrochemical devices will benefit from the present disclosure. For example, munitions, automatic external defibrillators and the like that contain high energy density capacitors often sit idle for months or years at a time before a first use and each such device can benefit from using capacitors fabricated according to the present invention.

Defibrillators are preferably an implantable device capable of monitoring certain aspects of the cardiovascular system and supplying a therapeutic charge based on indications therein. A defibrillator is illustrated schematically in FIG. 1 as generally indicated at 1. The comprises a case, 2, within which operational components are encased. The defibrillator comprises a controller, 3, capable of monitoring certain features of the cardiovascular system of the person within which the defibrillator is placed. Monitor leads, 4 and 5, relay patient information, such as heart rhythm, to the controller. The controller then determines the necessity for a therapeutic electrical pulse by any technique known in the art. When a therapeutic pulse is necessary the power module, 6, releases a pulse through pulse leads, 7 and 8. The monitor leads and pulse leads may be the same leads if desired.

Electrolytic capacitors, particularly tantalum electrolytic capacitors, fabricated so as to manifest a large capacitance density (i.e., high capacitance per unit volume) at intermediate use voltages (i.e., from about 150 volts to about 300 volts) are generally fabricated from powder metallurgy compacts. The compacts are sintered at appropriately high temperature and are then anodized in an anodizing electrolyte prior to assembly into finished capacitors. During the assembly operation each anode compact is impregnated with a working or fill electrolyte which serves to conduct current from the cathode surface of the device to the anode oxide dielectric. Once the anode body is impregnated with a working electrolyte, the device is sealed so as to prevent escape of the liquid electrolyte. The device is typically tested prior to being placed into service. The working electrolyte usually is characterized as having a much lower resistance and dissipation factor than anodizing electrolytes. One undesirable consequence of the relatively low electrical resistivity of the working electrolyte is that the breakdown voltage of the electrolyte, that is the maximum voltage which the electrolyte-anode oxide system will support regardless of the voltage to which the anode is formed (i.e., anodized), is generally significantly lower than that of appropriate anodizing electrolytes. Working electrolytes have to be chosen so as to have a sufficiently high breakdown voltage so as not to cause premature failure during the working life of the device.

The present invention is not limited by the working electrolyte but a particularly preferred working electrolyte comprises about 10-70%, by weight, a compound of formula 1, described wherein, about 0.05 to about 40%, by weight, ionogens such as ammonium acetate and/or acetic acid, at a pH of about 1 to about 7.

The capacitor comprises an oxide of a valve metal. The oxide is preferably formed by anodization in an anodizing electrolyte wherein the anodizing electrolyte comprises a class of amines containing alcohol groups, known as alkanolamines. Alkanolamines, generally have a boiling point sufficiently high (e.g., vapor pressure sufficiently low) for practical use in anodizing electrolytes. Particularly preferred alkanolamines include monoethanolamine, diethanolamine, triethanolamine, ethyldiethanolamine, diethylethanolamine, dimethylethanolamine, and dimethylaminoethoxy ethanol.

A particularly preferred anodizing electrolyte is an aqueous solution of an organic solvent in combination with phosphoric acid and one or more alkanolamines and having a nearly neutral pH. This anodizing electolyte is particularly useful for anodizing powder metallurgy valve metal anodes.

The organic solvent is preferably chosen from monomeric glycols, glycerine, polyethylene glycols, polyethylene glycol monomethyl ethers, polyethylene glycol dimethyl ethers, 2-methyl-1,3-propanediol, diethylene glycol, N-alkyl-2-pyrrolidones and mixtures thereof.

A particularly preferred organic solvent, for the anodizing electrolyte is at least one organic solvent selected from Formula 1:

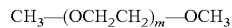   Formula 1 wherein m is an integer from 3 to 10.

More preferably the aqueous anodizing electrolyte comprises about 25 to about 70 wt % of the compound of Formula 1. In the compound of Formula 1, m is most preferably an integer of 4. When m is less than about 2 the compound is unstable over long-term use and when m is above about 10 the solubility of the compound may be undesirable.

A sufficient quantity of the alkanolamine is used to form an electrolyte having a near neutral pH of about 4 to about 9. The amount of alkanolamine is generally between about 0.1% and about 10%, by weight of the electrolytic solution.

The alkanolamine reacts with the phosphoric acid to form alkanolamine phosphate complexes. Solutions of alkanolamine phosphates in aqueous polyethylene glycol, polyethylene glycol mono methyl ether, and/or polyethylene glycol dimethyl ether may easily be formulated for low- or high-voltage anodizing of powder metallurgy compacts.

Phosphate-containing electrolytes formulated with alkanolamines tend to be non-corrosive to anodizing tanks, and not subject to the formation of polyphosphoric acid deposits inside powder metallurgy anodes during anodizing as is found with low pH (less than about 4), phosphate containing anodizing electrolytes. Thus, anodizing electrolytes containing alkanolamine phosphates in place of alkali metal phosphates greatly reduce the amount of phosphate deposits on the carrier bars which support the anodes. Further, the deposits which do form tend to dissolve much more readily during rinsing of the anodes after anodizing.

Low voltage powder metallurgy anodes are anodes anodized to less than about 100 to 150 volts and generally fabricated from valve metal powders having 0.35 m$^2$/gram or more surface area and a CV product of more than about 35,000 microcoulombs/gram with a solution temperature of approximately 20 to 50° C. For anodizing such low-voltage powder metallurgy anodes, about 5 to about 35%, by weight, preferably about 10 to about 25%, by weight, glycols, polyethylene glycol, polyethylene glycol mono methyl ether, and/or polyethylene glycol di methyl ether is combined with about 0.1% to about 2%, by weight phosphoric acid. A sufficient amount of an alkanolamine is added to give a pH of about 4 to about 9, preferably about 7. Although a wide range of phosphoric acid to alkanolamine ratio may be used, it is preferable that the ratio provide a near neutral pH.

High voltage powder metallurgy anodes are generally anodized above about 100 to 150 volts and fabricated from valve metal powder having less than about 0.35 m$^2$/gram or less than about 35,000 microcoulombs/gram. For anodizing such high-voltage powder metallurgy anodes, about 50 to about 70%, by weight, of one of glycols, polyethylene glycol, polyethylene glycol mono methyl ether, and/or polyethylene glycol di methyl ether is combined with about 0.1% to about 2%, by weight, phosphoric acid. A sufficient amount of an alkanolamine is added to provide a resistivity of about 500 ohm-cm to about 10,000 ohm-cm at about 20° C. to about 50° C.

For both low and high voltage anodes, the anodizing is typically carried out with a fixed current or a fixed rate of voltage rise until a preselected voltage is reached. Upon reaching this voltage, the anodes are held at voltage for a period of time to stabilize the anodic oxide. Such low- and high-voltage anodizing techniques are well known within the skill of the art.

A particularly preferred anode is fabricated from a high surface area metal powder. High surface area powder is defined as powder having at least 0.35 m$^2$/g or 35,000 CV/g, preferably at least 0.5 m$^2$/g or 50,000 CV/g.

The anodized anode, also referred to as an anode compact, is incorporated into an electrolytic capacitor.

The preferred aqueous anodizing solution of the present invention comprises about 0.05 to about 20%, by weight, ionogen and about 10 to about 70%, by weight, of at least one compound referred to in the art as polyethylene glycol dimethyl ethers and specifically defined by Formula 1. An additional acid may be included in an amount sufficient to maintain an acidic pH.

The anode material is a valve metal preferably chosen from titanium, tungsten, chromium, aluminium, zirconium, hafnium, zinc, vanadium, niobium, tantalum, bismuth, antimony and mixtures and alloys thereof. Tantalum is the most preferred anode material.

The cathode preferably comprises a conductive metal provided with a semiconductive or metal-like conductive coating. The coating can be carbon or an oxide, nitride or carbide of a metal. Suitable cathode metals include tantalum, titanium, nickel, iridium, platinum, palladium, gold, silver, cobalt, molybdenum, ruthenium, manganese, tungsten, iron, zirconium, hafnium, rhodium, vanadium, osmium and niobium. A particularly preferred cathode electrode comprises a porous ruthenium oxide film provided on a titanium substrate.

It is preferable that the working electrolyte be maintained at an acidic pH. Most preferably the electrolyte is maintained at a pH of about 1 to about 7. More preferably the pH is maintained at about 3-6. A pH of about 4-5 is most preferred.

As is known in the art, a separator material physically separates the anode and cathode from each other and the separator prevents electrical short circuits between the anode and cathode. The separator material is preferably unreactive with the anode, cathode and working electrolyte and is sufficiently porous to allow the working electrolyte to freely flow through the separator material. Suitable separators include woven and non-woven fabrics of polyolefinic fibers as known in the art.

While not restricted by any theory, the alkanolamine is thought to decrease the formation of polyphosphate on the surface of the oxide during formation. The minimization of polyphosphate ensures that the oxide thickness is more uniform and thereby sufficiently thick to minimize leakage current (e.g., thinner regions of an oxide layer can lead to higher leakage current). The phosphoric acid facilitates incorporation of phosphate into the oxide that is beneficial for chemical resistivity. The organic solvent allows the anodization to occur at lower temperatures which decreases oxidation of the amines The increased capacitor efficiency and reduced deformation both contribute to reduced charge time and reduced battery consumption. The capacitor therefore benefits from increased longevity and/or reduced battery volume. The inventive capacitor would demonstrate a charge time reduction from one to several seconds. The battery longevity would increase by about one year and the volume savings would be about 1-2 cc of device volume.

The invention has been described with particular emphasis on the preferred embodiments. It would be realized from the teachings herein that other embodiments, alterations, and configurations could be employed without departing from the scope of the invention which is more specifically set forth in the claims which are appended hereto.

The invention claimed is:

1. A method for fabricating a medical device comprising:
   forming a capacitor comprising the steps of:
   preparing a metal anode from a valve metal powder comprising anodizing the metal anode with an aqueous anodizing electrolyte comprising phosphoric acid, at least one organic solvent and alkanolamine;
   providing a cathode;
   activating said anode and said cathode with a working electrolyte;
   incorporating said capacitor into a circuit; and
   incorporating said circuit in said medical device without oxide reformation.

2. A method according to claim 1 wherein said anode comprises a metal selected from a group consisting of titanium, tungsten, chromium, aluminium, zirconium, hafnium, zinc, vanadium, niobium, bismuth, antimony and tantalum.

3. A method according to claim 2 wherein said anode is tantalum.

4. A method according to claim 1 wherein said cathode is a conductive metal provided with a semiconductive or metal-like conductive coating.

5. A method according to claim 4 wherein said cathode is at least one material chosen from a group consisting of carbon or an oxide, nitride, or carbide of a metal.

6. A method according to claim 5 wherein said cathode comprises a metal selected from a group consisting of tantalum, titanium, nickel, iridium, platinum, palladium, gold, silver, cobalt, molybdenum, ruthenium, manganese, tungsten, iron, zirconium, hafnium, rhodium, vanadium, osmium and niobium.

7. A method according to claim 6 wherein said cathode comprises a porous ruthenium oxide film provided on a titanium substrate.

8. A method according to claim 1 wherein said anodizing electrolyte has a pH of about 4 to about 9.

9. A method according to claim 1 wherein said anodizing electrolyte comprises about 0.1% to about 2.0%, by weight, phosphoric acid, about 1% to about 70%, by weight, of at least one organic solvent and about 0.1% to about 10%, by weight, of at least one alkanolamine.

10. A method according to claim 9 wherein said anodizing electrolyte comprises about 0.1% to about 6%, by weight, of said alkanolamine.

11. A method according to claim 9 wherein said anodizing electrolyte comprises about 5% to about 35%, by weight of said organic solvent.

12. A method according to claim 9 wherein said anodizing electrolyte comprises about 50% to about 70%, by weight of said organic solvent.

13. A method according to claim 1 wherein said organic solvent is selected from the group consisting of monomeric glycols, glycerine, polyethylene glycols, polyethylene glycol monomethyl ethers, polyethylene glycol dimethyl ethers, 2-methyl-1,3-propanediol, diethylene glycol, N-alkyl-2-pyrrolidones and mixtures thereof.

14. A method according to claim 13 wherein said organic solvent is a compound of Formula 1:

$$CH_3\text{---}(OCH_2CH_2)_m\text{---}OCH_3 \quad \text{Formula 1}$$

wherein m is an integer from 3 to 10.

15. A method according to claim 14 wherein said m is an integer from 3 to 5.

16. A method according to claim 15 wherein said m is 4.

17. A method according to claim 1 wherein said alkanolamine is selected from a group consisting of monoethanol amine, diethanol amine, triethanol amine, ethyl diethanolamine, diethyl ethanolamine, dimethyl ethanolamine and dimethyl amino ethoxy ethanol.

18. A method according to claim 1 comprising about 25 to about 50%, by weight, said organic solvent.

19. A method according to claim 1 wherein said anodizing electrolyte has a pH of about 3 to about 9.

\* \* \* \* \*